United States Patent [19]

Watanabe et al.

[11] Patent Number: 5,122,516

[45] Date of Patent: Jun. 16, 1992

[54] PREPARATION FOR BLOOD DIALYSIS AND METHOD FOR PRODUCTION THEREOF

[75] Inventors: Tomio Watanabe; Sawako Koyama; Kazuo Kawahara; Eiji Watanabe; Tatsuaki Umeki, all of Ashigarakami, Japan

[73] Assignee: Terumo Kabushiki Kaisha, Tokyo, Japan

[21] Appl. No.: 528,610

[22] Filed: May 25, 1990

[30] Foreign Application Priority Data

May 26, 1989 [JP] Japan .................................. 1-134339
May 26, 1989 [JP] Japan .................................. 1-134340
Jul. 6, 1989 [JP] Japan .................................. 1-173120

[51] Int. Cl.⁵ .......................... A61K 9/00; A61K 9/14; A61K 31/70
[52] U.S. Cl. ...................... 514/23; 210/646; 210/647; 514/832; 514/833
[58] Field of Search .......................... 514/23, 832, 833; 210/646, 647

[56] References Cited

U.S. PATENT DOCUMENTS

| | | | |
|---|---|---|---|
| 3,560,380 | 2/1971 | Stade | 210/647 |
| 3,660,280 | 5/1972 | Rogers | 210/646 |
| 3,911,915 | 10/1975 | Seifter et al. | 210/646 |
| 3,962,075 | 6/1976 | Fialkoff et al. | 210/647 |
| 4,326,955 | 4/1982 | Babb et al. | 210/646 |
| 4,489,535 | 12/1984 | Veltman | 210/646 |
| 4,655,941 | 4/1987 | Suzuki | 210/647 |
| 4,756,838 | 7/1988 | Veltman | 210/647 |
| 4,853,237 | 8/1989 | Prinkkila et al. | 514/23 |
| 4,886,789 | 12/1989 | Milner | 210/647 |
| 4,959,175 | 9/1990 | Yatzidis | 210/647 |

FOREIGN PATENT DOCUMENTS

| | | |
|---|---|---|
| 2924406 | 12/1980 | Fed. Rep. of Germany . |
| 58-27246 | 6/1983 | Japan . |
| 62-30540 | 2/1987 | Japan . |
| 2025787 | 1/1980 | United Kingdom . |

*Primary Examiner*—Ronald W. Griffin
*Attorney, Agent, or Firm*—Burns, Doane, Swecker & Mathis

[57] ABSTRACT

A preparation for blood dialysis comprising two composition, i.e. a first powdery composition comprising (a) solid electrolytes for dialysis and a liquid acid, (b) solid electrolytes for dialysis, glucose and a liquid acid, or (c) solid inorganic salts for dialysis, glucose, sodium acetate and acetic acid, and a second composition comprising (a) sodium hydrogen carbonate and glucose, (b) sodium carbonate, or (c) sodium hydrogen carbonate and sodium acetate.

25 Claims, No Drawings

PREPARATION FOR BLOOD DIALYSIS AND METHOD FOR PRODUCTION THEREOF

BACKGROUND OF THE INVENTION

1. Field of the Invention

The present invention relates to a preparation for blood dialysis and a method for the production thereof. More particularly, it relates to a uniform powdery preparation for blood dialysis excellent in stability of storage and a method for the production thereof.

2. Description of the Prior Art

In the performance of blood dialysis, the patient's blood is purified in the artificial kidney. Inside the artificial kidney, the purification of the blood is effected by keeping the dialytic solution circulated in the artificial kidney, allowing the dialytic solution to contact the blood through the medium of a permeable membrane, and causing the waste matter and water accompanied by the blood to pass into the dialytic solution. The dialytic solution is closely and impartibly related to the improvement of the artificial kidney in performance. The acetate dialytic solution, the leader of the conventional dialytic solutions, is such that owing to the advance of the artificial kidney in quality, the acetic acid allowed to pass from this dialytic solution into the patient's vital organs has gained in quantity and the acetic acid causes the patient to suffer from such displeasing symptoms as headache and hypotension. Thus, it is giving place to the bicarbonate dialytic solution which exerts no appreciable burden upon the patient.

Unlike the acetate dialytic solution, the bicarbonate dialytic solution cannot be prepared as a single-component dope because sodium hydrogen carbonate present therein, on reaction with calcium or magnesium, gives rise to a precipitate. The bicarbonate dialytic solution, therefore, is prepared as a two-component composition comprising sodium hydrogen carbonate (principal solution) and a component containing calcium, magnesium, sodium, etc. (formulating liquid).

The principal component is prepared in the form of powder or solution and the formulating component in the form of solution. The amount of the principal component to be used is in the range of 500 to 1,000 g as powder or 10 to 12 liters as liquid and that of the formulating component in the range of 9 to 12 liters as liquid respectively per patient. In an institute abounding in patients, the work of transferring storage tanks of the dialytic solution exerts a heavy burden on workers. In an institute capable of performing dialysis simultaneously on 20 patients, for example, the dopes of both principal component and formulating component in a total amount enough for 40 patients (about 380 to 480 kg) must be transferred. The institute suffers also from the problem that the transfer and storage of these dopes call for engagement of human labor and require preservation of floor spaces.

In the light of the true state of affairs described above, efforts are directed to decreasing the weight of the dialytic preparation by producing this preparation in the form of powder. JP-B-58-27,246 (1983), for example, discloses as means for uniform dispersion of a liquid acid a method for producing an electrolytic compound powder of the bicarbonate dialysis quality by powder mixing using a microfine powder of sodium chloride acidified with acetic acid. JP-A-62-30,540 (1987), concerning the production of a preparation for dialysis using sodium acetate as a principal component, discloses a technique for decreasing dispersion of the contents of such microconstituents as $MgCl_2 \cdot 6H_2O$ and $CaCl_2 \cdot 2H_2O$ in the dialytic solution obtained from a dialytic preparation having sodium acetate as a principal component by intimately mixing these microconstituents with sodium acetate and water and converting the resultant mixture into fine powder.

In the powdery preparation for dialysis of the type using sodium hydrogen carbonate as a principal component, calcium chloride and magnesium chloride exhibit a deliquescing property and sodium chloride possibly acquires enhanced hygroscopicity in the presence of calcium chloride and magnesium chloride. This preparation, therefore, undergoes deliquescence or solidification during the course of production, transfer, or storage and entails the disadvantage that it betrays notable dispersion of composition and inferior stability during protracted preservation. Further, since this preparation uses acetic acid as a liquid acid, it possesses a high vapor pressure and readily succumbs to volatilization even when it is adsorbed on an inorganic salt, and lacks stability and workability. In recent years, the practice of curbing possible variation in the blood sugar level by adding glucose to the dialytic solution has been finding acceptance in the field of clinical medicine. None of the preparations heretofore produced for dialysis has proved to be capable of retaining stability in protracted preservation.

An object of this invention, therefore, is to provide a novel powdery preparation for dialysis and a method for the production thereof.

Another object of this invention is to provide a powdery preparation for dialysis, which excels in the ability to withstand the impact of transfer and storage and in the maintenance of uniformity and stability of powder production.

SUMMARY OF THE INVENTION

The objects described above are accomplished by a preparation for blood dialysis, comprising two compositions, i.e. a first powdery composition comprising solid electrolytes for dialysis and a liquid acid and a second powdery composition comprising sodium hydrogen carbonate and glucose.

The present invention discloses a preparation for blood dialysis, wherein the liquid acid is acetic acid. The present invention further discloses a preparation for blood dialysis, wherein the acetic acid has been incorporated by impregnation in a pelletized solid acetate-containing electrolyte for dialysis. The present invention further discloses a preparation for blood dialysis, wherein the preparation, on being dissolved in a prescribed amount of water, produces the following components of solid electrolytes for dialysis and liquid acid from the first composition:

| | |
|---|---|
| $Na^+$ | 90 to 140 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 90 to 140 mmols |
| $CH_3COO^-$ | 6 to 15 mmols | and the following components of sodium hydrogen carbonate and glucose from the second composition:

| | |
|---|---|
| Na⁻ | 15 to 40 mmols |
| HCO₃⁻ | 15 to 40 mmols |
| Glucose | 4 to 12 mmols |

The present invention further discloses a preparation for blood dialysis, wherein the second solid composition for dialysis is contained in combination with a desiccator such as a moisture absorbent in a moistureproof packing material possessing moisture permeability (20° C.) of not more than 2.0 g/m²·24hrs. The present invention further discloses a preparation for blood dialysis, wherein the first solid composition for dialysis is contained in combination with a desiccator such as a moisture absorbent in a moistureproof packing material possessing moisture permeability (20° C.) of not more than 2.0 g/m²·24hrs.

The objects described above are accomplished by a method for the production of a preparation for blood dialysis, comprising two compositions, i.e. a first powdery composition comprising solid electrolytes for dialysis and a liquid acid and a second powdery composition comprising sodium hydrogen carbonate and glucose, which method is characterized by the fact that the first composition is produced by mixing the components of the solid electrolytes for dialysis, pulverizing and granulating the resultant mixture, and subsequently mixing the resultant granules with the liquid acid.

The objects are further accomplished by a method for the production of a preparation for blood dialysis, comprising two compositions, i.e. a first powdery composition comprising solid electrolytes for dialysis and a liquid acid and a second powdery composition comprising sodium hydrogen carbonate and glucose, which method is characterized by the fact that the first composition is produced by spraying an aqueous solution of the components of the solid electrolytes for dialysis except for sodium chloride into a fluidized bed of sodium chloride powder and, at the same time, granulating the wet sodium chloride powder, and mixing the resultant granules with the liquid acid.

The present invention further discloses a method for the production of a preparation for blood dialysis, wherein the second composition is produced by mixing the powder of glucose, for example, with sodium hydrogen carbonate and subsequently granulating the resultant mixture.

The objects are further accomplished by a preparation for blood dialysis comprising two compositions, i.e. a first powdery composition comprising solid electrolytes for dialysis, glucose, and a liquid acid and a second powdery composition comprising sodium hydrogen carbonate.

The present invention discloses a preparation for blood dialysis, wherein the liquid acid is acetic acid. The present invention further discloses a preparation for blood dialysis, wherein the acetic acid is specifically adsorbed on granules of the solid sodium acetate-containing electrolytes for dialysis. The present invention further discloses a preparation for blood dialysis, wherein the preparation, on being dissolved in a prescribed amount of water, produces the following components of solid electrolytes for dialysis, glucose, and liquid acid from the first composition:

| | |
|---|---|
| Na⁺ | 90 to 140 mmols |

| | |
|---|---|
| K⁻ | 0 to 4 mmols |
| Ca⁻⁻ | 0.5 to 2.2 mmols |
| Mg⁺⁺ | 0.2 to 1.0 mmol |
| Cl⁻ | 90 to 140 mmols |
| CH₃COO⁻ | 6 to 15 mmols |
| Glucose | 4 to 12 mmols | and the following components of sodium hydrogen carbonate from the second composition:

| | |
|---|---|
| Na⁺ | 15 to 40 mmols |
| HCO₃⁻ | 15 to 40 mmols |

The present invention further discloses a preparation for blood dialysis, wherein the first solid composition for dialysis and a desiccant (moisture absorbent) are contained in a moistureproof packing material having moisture permeability (20° C.) of not more than 2.0 g/cm²·24hrs.

The objects described above are further accomplished by a method for the production of a preparation for blood dialysis comprising two compositions, i.e. a first powdery composition comprising solid electrolytes for dialysis, glucose, and a liquid acid and a second powdery composition comprising sodium hydrogen carbonate.

The present invention discloses a preparation for blood dialysis, wherein the liquid acid is acetic acid, which method is characterized by the fact that the first composition is produced by mixing the components of the solid electrolytes for dialysis and glucose, pulverizing and granulating the resultant mixture, and subsequently mixing the resultant granules with the liquid acid.

These objects are further accomplished by a method for the production of a preparation for blood dialysis comprising two compositions, i.e. a first powdery composition comprising solid electrolytes for dialysis, glucose, and a liquid acid and a second powdery composition comprising sodium hydrogen carbonate.

The present invention discloses a preparation for blood dialysis, wherein the liquid acid is acetic acid, which method is characterized by the fact that the first composition is produced by spraying an aqueous solution of the components of the solid electrolytes for dialysis other than sodium chloride into a fluidized bed of a mixed powder of sodium chloride and glucose and, at the same time, granulating the wet mixed powder, and mixing the resultant granules with the liquid acid.

These objects are further accomplished by a preparation for blood dialysis comprising two compositions, i.e. a first powdery composition comprising solid inorganic salts for dialysis, glucose, sodium acetate, and acetic acid and a second powdery composition comprising sodium hydrogen carbonate and sodium acetate.

The present invention further discloses a preparation for blood dialysis, wherein the preparation on being dissolved in a prescribed amount of water produces the following components of solid inorganic salts for dialysis, glucose, sodium acetate, and acetic acid from the first composition:

| | |
|---|---|
| Na⁺ | 85 to 135 mmols |
| K⁺ | 0 to 4 mmols |
| Ca⁺⁺ | 0.5 to 2.2 mmols |
| Mg⁺⁺ | 0.2 to 1.0 mmol |

-continued

| | |
|---|---|
| $Cl^-$ | 90 to 140 mmols |
| $CH_3COO^-$ | 4 to 10 mmols |
| Glucose | 4 to 12 mmols | and the following components of sodium hydrogen carbonate and sodium acetate from the second composition:

| | |
|---|---|
| $Na^+$ | 15 to 40 mmols |
| $HCO_3^-$ | 15 to 40 mmols |
| $CH_3COO^-$ | 0.5 to 3 mmols |

The present invention further discloses a preparation for blood dialysis, wherein the second composition contains sodium chloride.

The present invention further discloses a preparation for blood dialysis, wherein the preparation on being dissolved in a prescribed amount of water produces the following components of solid inorganic salts for dialysis, glucose, sodium acetate, and acetic acid from the first composition:

| | |
|---|---|
| $Na^+$ | 6 to 135 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 4 to 140 mmols |
| $CH_3COO^-$ | 4 to 10 mmols |
| Glucose | 4 to 12 mmols | and the following components of sodium hydrogen carbonate, sodium acetate, and sodium chloride from the second composition:

| | |
|---|---|
| $Na^+$ | 15 to 135 mmols |
| $Cl^-$ | 1 to 120 mmols |
| $HCO_3^-$ | 15 to 40 mmols |
| $CH_3COO^-$ | 0.5 to 3 mmols |

The objects described above are further accomplished by a method for the production of a preparation for blood dialysis comprising two compositions, i.e. a first powdery composition comprising solid inorganic salts for dialysis, glucose, sodium acetate, and acetic acid and a second powdery composition comprising sodium hydrogen carbonate and sodium acetate, which method is characterized by the fact that the first composition is produced by mixing the components of the solid inorganic salts for dialysis, sodium acetate, and glucose, pulverizing and then granulating the resultant mixture, and mixing the resultant granules with acetic acid.

These objects are further accomplished by a method for the production of a preparation for blood dialysis comprising two compositions, i.e. a first powdery composition comprising solid inorganic salts for dialysis, glucose, sodium acetate, and acetic acid and a second powdery composition comprising sodium hydrogen carbonate and sodium acetate, which method is characterized by the fact that the first composition is produced by spraying an aqueous solution of the components of the solid inorganic salts for dialysis excluding sodium chloride and containing or not containing sodium acetate into a fluidized bed of a mixed powder consisting of sodium chloride and glucose and not containing or containing sodium acetate and, at the same time, granulating the wet mixed powder, and mixing the resultant granules with acetic acid.

Further, the present invention discloses a method for the production of a preparation for blood dialysis, wherein the second composition is produced by mixing sodium acetate powder or mixed powder of sodium acetate and sodium chloride with sodium hydrogen carbonate and subsequently granulating the resultant mixture.

EXPLANATION OF THE PREFERRED EMBODIMENT

The preparation for blood dialysis according with the present invention comprises two compositions, i.e. a first powdery composition comprising solid electrolytes for dialysis and a liquid acid and a second powdery composition comprising sodium hydrogen carbonate and glucose.

The solid electrolytes for dialysis which are usable for the first composition include sodium chloride, potassium chloride, calcium chloride, magnesium chloride, and sodium acetate, for example. The liquid acid is used as a pH-adjusting agent. The liquid acids which are usable for this purpose include acetic acid, lactic acid, and hydrochloric acid, for example. Among other liquid acids mentioned above acetic acid proves to be particularly preferable. This acetic acid is generally adsorbed specifically by the granules of the solid electrolyte for dialysis, particularly by the sodium acetate contained in the granules.

The first composition is preferable, on being dissolved in a prescribed amount of water, to produce the following components of solid electrolytes for dialysis and liquid acid:

| | |
|---|---|
| $Na^+$ | 90 to 140 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 90 to 140 mmols |
| $CH_3COO^-$ | 6 to 15 mmols |
| preferably: | |
| $Na^+$ | 100 to 130 mmols |
| $K^+$ | 1.5 to 3 mmols |
| $Ca^{++}$ | 0.75 to 1.8 mmols |
| $Mg^{++}$ | 0.3 to 0.8 mmol |
| $Cl^-$ | 100 to 130 mmols |
| $CH_3COO^-$ | 8 to 12 mmols |

The average particle size of the first composition is in the range of 10 to 200 mesh, preferably 14 to 100 mesh, of standard sieves.

The first composition is preferably produced by either the dry method or the fluidized-bed method.

By the dry method, the first composition is obtained by stirring and mixing the solid electrolytes for dialysis with a stirring and mixing device such as a vertical granulator, for example, then pulverizing the mixed solid electrolytes with a pulverizing device such as a pin mill, mixing the pulverized solid electrolytes with a stirring and mixing device such as a vertical granulator, for example, granulating the resultant mixture with a dry granulating device such as a roller compacter, for example, combining the resultant granules with the liquid acid, and mixing them with a stirring and mixing them with a stirring and mixing device such as a vertical granulator or a Nauter mixer, for example.

By the fluidized-bed method, the first composition is obtained by dissolving the solid electrolytes for dialysis other than sodium chloride in water of an amount 0.8 to 30 times, preferably 1.5 to 15 times, the amount of the solid electrolytes, spraying the resultant aqueous solution into a fluidized bed formed of sodium chloride powder inside a fluidized-bed granulating device and, at the same time, granulating the wet powder, combining the resultant granules with the liquid acid, and mixing them with a stirring and mixing device such as a vertical granulator or a Nauter mixer, for example.

The second composition is a powder comprising sodium hydrogen carbonate and glucose. When this second composition is dissolved in a prescribed amount of water, the components thereof, i.e. sodium hydrogen carbonate and glucose produce 15 to 40 mmols of $Na^+$, 15 to 40 mmols of $HCO_3^-$, and 4 to 12 mmols of glucose, preferably 20 to 27 mmols of $Na^+$, 20 to 27 mmols of $HCO_3^-$, and 6 to 100 mmols of glucose. The average particle size of the second composition is in the range of 10 to 100 mesh, preferably 12 to 100 mesh, of standard sieves.

The second composition is obtained by pulverizing glucose with a pulverizing device such as a pin mill, for example, mixing the pulverized glucose with sodium hydrogen carbonate powder in a stirring and mixing device such as a vertical granulator, for example, and subsequently granulating the resultant mixture in a dry granulating device such as a roller compacter, for example.

The first and second compositions which are produced as described above are placed in separate containers. Prior to use, these compositions are dissolved in water and the resultant aqueous solution is supplied to the artificial kidney, there to be used as a liquid for blood dialysis.

The packing material, to be used for containing these compositions preferably possesses low moisture permeability. It is preferable, for example, to use a moisture-proof packing material possessing moisture permeability (20° C.) of not more than 2.0 $g/m^2 \cdot 24hrs$. As one packing material fulfilling this requirement, there may be cited a laminate film which is obtained by superposing polyethylene terephthalate/polyethylene /aluminum foil/polyethylene layers measuring 12 $\mu m$, 15 $\mu m$, 7 $\mu m$, and 30 $\mu m$ respectively in thickness (moisture permeability 0.1 $g/m^2 \cdot 24hrs$). The first and second compositions are preferably each contained in a packing material in combination with an air-permeability container filled with a desiccant such as silica gel, a synthetic zeolite type moisture absorbent, or a calcium carbonate type moisture absorbent, for example.

The preparation for blood dialysis according with the present invention comprises two compositions, i.e. a first powdery composition comprising solid electrolytes for dialysis, glucose, and a liquid acid and a second powdery composition comprising sodium hydrogen carbonate.

The solid electrolytes for dialysis which are usable for the first composition include sodium chloride, potassium chloride, calcium chloride magnesium chloride, and sodium acetate, for example. The liquid acid is used as a pH-adjusting agent. The liquid acids which are usable for this purpose include acetic acid, lactic acid, and hydrochloric acid, for example. Among other liquid acids mentioned above, acetic acid proves to be particularly desirable. This acetic acid is generally adsorbed specifically by the granules of the solid electrolyte for dialysis, particularly by the sodium acetate contained in the granules.

The first composition preferably, on being dissolved in a prescribed amount of water, produces the following components of solid electrolytes for dialysis and liquid acid:

| | | |
|---|---|---|
| $Na^+$ | 90 to 140 | mmols |
| $K^+$ | 0 to 4 | mmols |
| $Ca^{++}$ | 0.5 to 2.2 | mmols |
| $Mg^{++}$ | 0.2 to 1.0 | mmol |
| $Cl^-$ | 90 to 140 | mmols |
| $CH_3COO^-$ | 6 to 15 | mmols |
| Glucose | 4 to 12 | mmols |
| perferably: | | |
| $Na^+$ | 100 to 130 | mmols |
| $K^+$ | 1.5 to 3 | mmols |
| $Ca^{++}$ | 0.75 to 1.8 | mmols |
| $Mg^{++}$ | 0.3 to 0.8 | mmol |
| $Cl^-$ | 100 to 130 | mmols |
| $CH_3COO^-$ | 8 to 12 | mmols |
| Glucose | 6 to 10 | mmols |

The average particle size of the first composition is in the range of 10 to 200 mesh, preferably 14 to 100 mesh, of standard sieves.

The first composition is desired to be produced by either the dry method or the fluidized-bed method.

By the dry method, the first composition is obtained by stirring and mixing the solid electrolytes for dialysis and glucose with a stirring and mixing device such as a vertical granulator, for example, then pulverizing the mixed solid electrolytes with a pulverizing device such as a pin mill mixing the pulverized solid electrolytes with a stirring and mixing device such as a vertical granulator, for example, granulating the resultant mixture with a dry granulating device such as a roller compacter, for example, combining the resultant granules with the liquid acid, and mixing them with a stirring and mixing them with a stirring and mixing device such as a vertical granulator or a Nauter mixer, for example.

By the fluidized-bed method, the first composition is obtained by dissolving the solid electrolytes for dialysis other than sodium chloride in water of an amount 0.8 to 30 times, preferably 1.5 to 15 times, the amount of the solid electrolytes, spraying the resultant aqueous solution into a fluidized bed from of a mixed powder of sodium chloride and glucose powder inside a fluidized-bed granulating device and, at the same time, granulating the wet powder, combining the resultant granules with the liquid acid, and mixing them with a stirring and mixing device such as a vertical granulator or a Nauter mixer, for example. The mixed powder of sodium chloride and glucose is obtained, for example, by mixing them with a stirring and mixing device such as a vertical granulator a Nauter mixed.

The second composition is a powder comprising sodium hydrogen carbonate. When this second composition is dissolved in a prescribed amount of water, the sodium hydrogen carbonate produces 15 to 40 mmols of $Na^+$ and 15 to 40 mmols of $HCO_3^-$, preferably 20 to 30 mmols of $Na^+$ and 20 to 30 mmols of $HCO_3^-$. The average particle size of the second composition is not more than 500 $\mu m$, preferably in the range of 200 to 10 $\mu m$.

The first and second compositions which are produced as described above are placed in separate containers. Prior to use, these compositions are dissolved in water and the resultant aqueous solution is supplied to the artificial kidney, there to be used as a liquid for blood dialysis.

The packing material to be used for containing these compositions is as already described. The first and second compositions are preferably each contained in a packing material in combination with an air-permeable container filled with a desiccator such as silica gel, a synthetic zeolite type moisture absorbent, or a calcium carbonate type moisture absorbent.

The preparation for blood dialysis according with the present invention comprises two compositions, i.e. a first powdery composition comprising solid inorganic salts for dialysis, glucose, sodium acetate, and acetic acid and a second composition comprising sodium hydrogen carbonate and sodium acetate.

The solid inorganic salts for dialysis which are used in the first composition are preferably readily soluble in water. The solid inorganic salts which fulfil this requirement include sodium chloride, potassium chloride, calcium chloride, magnesium chloride, and sodium acetate, for example.

When the first composition is dissolved in a prescribed amount of water, the solid inorganic salts for dialysis, glucose, sodium acetate, and acetic acid preferably produce the following components:

| | |
|---|---|
| $Na^+$ | 85 to 135 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 90 to 140 mmols |
| $CH_3COO^-$ | 4 to 10 mmols |
| Glucose | 4 to 12 mmols |
| preferably | |
| $Na^+$ | 95 to 125 mmols |
| $K^+$ | 1.5 to 3 mmols |
| $Ca^{++}$ | 0.75 to 1.8 mmols |
| $Mg^{++}$ | 0.3 to 0.8 mmol |
| $Cl^-$ | 100 to 130 mmols |
| $CH_3COO^-$ | 5 to 9 mmols |
| Glucose | 6 to 10 mmols |

Where the second composition is used in combination with a sodium chloride-containing composition as described specifically herein below, the first composition is such that when it is dissolved in a prescribed amount of water, the solid inorganic salts for dialysis, glucose, sodium acetate, and acetic acid preferably produces the following components:

| | |
|---|---|
| $Na^+$ | 6 to 135 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 4 to 140 mmols |
| $CH_3COO^-$ | 4 to 10 mmols |
| Glucose | 4 to 12 mmols |
| preferably | |
| $Na^+$ | 30 to 100 mmols |
| $K^+$ | 1.5 to 3 mmols |
| $Ca^{++}$ | 0.75 to 1.8 mmols |
| $Mg^{++}$ | 0.3 to 0.8 mmol |
| $Cl^-$ | 100 to 130 mmols |
| $CH_3COO^-$ | 5 to 9 mmols |
| Glucose | 6 to 10 mmols |

The average particle size of the first composition is in the range of 10 to 200 mesh, preferably 14 to 100 mesh, of standard sieves.

The first composition is preferably produced by either the dry method or the fluidized-bed method.

By the dry method, the first composition is obtained by stirring and mixing the solid inorganic salts for dialysis and sodium acetate with a stirring and mixing device such as a vertical granulator, for example, then pulverizing the mixed solid electrolytes with a pulverizing device such as a pin mill, mixing the pulverized solid electrolytes with a stirring and mixing device such as a vertical granulator, for example, granulating the resultant mixture with a dry granulating device such as a roller compacter, for example, combining the resultant granules with acetic acid, and mixing them with a stirring and mixing device such as a vertical granulator or a Nauter mixer, for example.

By the fluidized-bed method, the first composition is obtained by dissolving the solid inorganic salts for dialysis other than sodium chloride in water of an amount 0.8 to 30 times, preferably 1.5 to 15 times, the amount of the solid inorganic salts, spraying the resultant aqueous solution into a fluidized bed formed of a mixed powder of sodium chloride and glucose inside a fluidized-bed granulating device and, at the same time, granulating the wet powder, combining the resultant granules with acetic acid, and mixing them with a stirring and mixing device such as a vertical granulator or a Nauter mixer, for example. In this case, sodium acetate may be incorporated into the aqueous solution, into the mixed powder of sodium chloride and glucose, or to both of them.

The second composition is a powdery composition comprising sodium hydrogen carbonate and sodium acetate. When this second composition is dissolved in a prescribed amount of water, the components thereof, i.e. sodium hydrogen carbonate and sodium acetate, produce 15 to 40 mmols of $Na^+$, 15 to 40 mmols of $HCO_3^-$, and 0.5 to 3 mmols of $CH_3COO^-$, preferably 18 to 32 mmols of $Na^+$, 18 to 35 mmols of $HCO_3^-$, and 0.8 to 2.5 mmols of $CH_3COO^-$. Where the second composition additionally incorporates therein sodium chloride, it is preferable that when the composition is dissolved in a prescribed amount of water, the components thereof, i.e. sodium hydrogen carbonate, sodium acetate, and sodium chloride, produce 15 to 135 mmols of $Na^+$, 1 to 120 mmols of $Cl^-$, 15 to 40 mmols of $HCO_3^-$, and 0.5 to 3 mmols of $CH_3COO^-$, preferably 40 to 120 mmols of $Na^+$, 35 to 115 mmols of $Cl^-$, 20 to 35 mmols of $HCO_3$, and 0.8 to 2.5 mmols of $CH_3COO^-$.

The second composition is obtained by mixing sodium acetate powder or a mixed powder of sodium acetate and sodium chloride with sodium hydrogen carbonate powder within a mixing device such as a vertical granulator and then granulating the resultant mixture in a dry granulating device such as a roller compacter.

The first and second compositions which are produced as described above are placed in separate containers. Prior to use, these compositions are dissolved in water and the resultant aqueous solution is supplied to the artificial kidney, there to be used as a liquid for blood dialysis.

The packing material to be used for containing these compositions preferably possesses low moisture permeability. It is preferable, for example, to use a moisture-proof packing material possessing moisture permeability (20° C.) of not more than 2.0 g/m²·24hrs. As one packing material fulfilling this requirement, there may be cited a laminate film which is obtained by superposing polyethylene terephthalate/polyethylene/aluminum foil/polyethylene layers measuring 12 μm, 15 μm, 7 μm, and 30 μm respectively in thickness (moisture permeability 0.1 g/m²·24hrs.

Now, the present invention will be described more specifically below with reference to working examples. Wherever the term "parts" is used in the working examples, it is meant as "parts by weight" unless otherwise specified.

EXAMPLE 1

In a vertical granulator (stirring and mixing device produced by Fuji Sangyo K.K. and marketed under product code of "VG-25P), 2188.7 parts of sodium chloride, 52.2 parts of potassium chloride, 77.2 parts of calcium chloride [CaCl$_2$·2H$_2$O], 35.6 parts of magnesium chloride [MgCl$_2$·6H$_2$O], and 215.2 parts of sodium acetate [CH$_3$COONa·3H$_2$O] were mixed by stirring. The resultant mixture was pulverized with a pin mill (pulverizer produced by Fuji Sangyo K.K. and marketed under trademark designation of "Kollplex 16Z") and further mixed by stirring with the vertical granulator. The mixture thus produced was pelletized with a roller compacter (dry pelletizer produced by Turbo Kogyo K.K. and marketed under product code of "WP-160X60"). The granules consequently obtained and 41.5 parts of acetic acid added thereto were mixed by stirring with the vertical granulator. The first composition obtained as the result was found to have a particle size distribution as follows.

| Mesh | % |
| --- | --- |
| -12 | 0.15 |
| 12-32 | 44.59 |
| 32-48 | 16.09 |
| 48-80 | 8.00 |
| 80-150 | 5.27 |
| 150- | 25.89 |
| Average particle diameter | 32-48 meshes |

EXAMPLE 2

An aqueous solution was obtained by dissolving 52.2 parts of potassium chloride, 77.2 parts of calcium chloride [CaCl$_2$·2H$_2$O], 35.6 parts of magnesium chloride [MgCl$_2$·6H$_2$O], and 357.2 parts of sodium acetate [CH$_2$COONa·3H$_2$O] in 1,500 parts (about 3 times the amount of electrolytes) of water. Inside a fluidized-bed pelletizer (produced by Fuji Sangyo K.K. and marketed under product code of "STREA-15"), 2188.7 parts of sodium chloride was fluidized and the fluidized bed of sodium chloride was sprayed with the aqueous solution mentioned above to gain in weight. The granules thus obtained were placed in the vertical granulator and were mixed by stirring with 41.5 parts of acetic acid added thereto. The first composition thus obtained was found to have a particle size distribution as follows.

| Mesh | % |
| --- | --- |
| -12 | 0.07 |
| 12-32 | 5.44 |
| 32-48 | 6.22 |
| 48-80 | 24.51 |
| 80-150 | 48.64 |
| 150- | 15.08 |
| Average particle diameter | 80-150 meshes |

EXAMPLE 3

In a pin mill, 525 parts of glucose was pulverized. The powder thus obtained was placed in the vertical granulator and were mixed by stirring with 750 parts of sodium hydrogen carbonate. The resultant mixture was pelletized with a roller compacter. The second composition consequently obtained was found to have a particle diameter distribution as follows.

| Mesh | % |
| --- | --- |
| -12 | 10.44 |
| 12-32 | 53.20 |
| 32-48 | 6.17 |
| 48-80 | 3.29 |
| 80-150 | 2.71 |
| 150- | 24.19 |
| Average particle diameter | 12-32 meshes |

EXAMPLE 4

The first and second composition obtained in Examples 2 and 3 were separately placed in bags of a laminate film obtained by superposing polyethylene terephthalate (12 μm), polyethylene (15 μm), aluminum foil (7 μm), and polyethylene (30 μm) layers without use of any desiccant and tested for stability in storage at 40° C. The results were as shown in Table 1.

TABLE 1

| Item | 0 month | 1 month | 2 months |
| --- | --- | --- | --- |
| First composition | | | |
| Color difference (ΔE) | 0.00 | 0.13 | 0.12 |
| Residual ratio of acetic acid ion (%) | 100.0 | 102.4 | 100.7 |
| Occurrence of aggregation | | Yes | Yes |
| Second composition | | | |
| Color difference (ΔE) | 0.00 | 1.28 | 2.36 |
| Occurrence of aggregation | | Yes | Yes |

The "color difference (ΔE)" represents the numerical value (absolute number) determined by the use of a colorimetric system (produced by Minolta Camera K.K. and marketed under product code of "CD-200"). The "residual ratio of acetic acid ion" represents the magnitude determined by dissolving part of a sample in water and examining the resultant aqueous solution by high-speed liquid chromatography (by the use of a system produced by Nippon Bunko K.K. and marketed under product code of "BIP-I").

EXAMPLE 5

The first and second compositions obtained in Examples 2 and 3 were separately placed in combination with silica gel as a desiccant in bags made of a laminate film obtained by superposing polyethylene terephthalate (12 μm), polyethylene (15 μm), aluminum foil (7 μm), and polyethylene (30 μm) layers and tested for stability in storage at 40° C. The results were as shown in Table 2.

TABLE 2

| Item | 0 month | 1 month | 2 months |
| --- | --- | --- | --- |
| First composition | | | |
| Color difference (ΔE) | 0.00 | 0.12 | 0.12 |
| Residual ratio of acetic acid ion (%) | 100.0 | 101.4 | 100.5 |
| Occurrence of aggregation | | No | No |

TABLE 2-continued

| Item | 0 month | 1 month | 2 months |
|---|---|---|---|
| Second composition | | | |
| Color difference (ΔE) | 0.00 | 0.12 | 0.06 |
| Occurrence of aggregation | | No | No |

EXAMPLE 6

The first composition obtained in Example 1, a composition produced by following the procedure of Example 1, except that the addition of sodium acetate was omitted (composition of Control 1), and a mixture of 2188.7 g of sodium chloride and 41.5 g of acetic acid (composition of Control 2) were left standing in the open air at 30° C. for 30 minutes and then analyzed to determine the residual ratio of acetic acid. The results were as shown in Table 3.

TABLE 3

| | Composition | | |
|---|---|---|---|
| Time | Example 1 | Control 1 | Control 2 |
| Immediately after production | 100% | 100% | 100% |
| After 30 minutes following production | 99.8% | 21.3% | 12.7% |

It is clearly noted from Table 3 that the preparations for blood dialysis according with the present invention show specific adsorption of acetic acid by sodium acetate and excel in stability in preservation.

EXAMPLE 7

In a vertical granulator (stirring and mixing device produced by Fuji Sangyo K.K. and marketed under product code of "VG-25P"), 2188.7 parts of sodium chloride, 52.2 parts of potassium chloride, 77.2 parts of calcium chloride [$CaCl_2 \cdot 2H_2O$], 35.6 parts of magnesium chloride [$MgCl_2 \cdot 6H_2O$], 215.3 parts of sodium acetate [$CH_3COONa \cdot 3H_2O$], and 525 parts of glucose were mixed by stirring. Then, the resultant mixture was pulverized with a pin mill (pulverizing device produced by Fuji Sangyo K.K. and marketed under trademark designation of "Kollplex 16Z"), and further mixed by stirring with the vertical granulator. The resultant mixture was pelletized with a roller compacter (dry granulating device produced by Turbo Kogyo K.K. and marketed under product code of "WP-160X60"). The granules and 41.5 parts of acetic acid added thereto were mixed by stirring with the vertical granulator. The first composition consequently obtained was found to have a particle size distribution as follows.

| Mesh | % |
|---|---|
| −12 | 7.79 |
| 12–32 | 51.41 |
| 32–48 | 6.70 |
| 48–80 | 3.56 |
| 80–150 | 2.75 |
| 150− | 27.82 |
| Average particle diameter | 12–32 meshes |

Separately, powdery sodium hydrogen carbonate was prepared as the second composition.

EXAMPLE 8

An aqueous solution was obtained by dissolving 52.2 parts of potassium chloride, 77.2 parts of calcium chloride [$CaCl_2 \cdot 2H_2O$], 35.6 parts of magnesium chloride [$MgCl_2 \cdot 6H_2O$], 357.2 parts of sodium acetate [$CH_3COONa \cdot 3H_2O$] in water of an amount 5 times the amount of the inorganic salts. Separately, granules obtained by mixing by stirring 2188.7 parts of sodium chloride and 525 parts of glucose with the vertical granulator were fluidized within a fluidized-bed pelletizer (produced by Fuji Sangyo K.K. and marketed under product code of "STREA-15") and the fluidized bed of the granules was sprayed with the aforementioned aqueous solution to gain in weight. The granules thus obtained were placed in the vertical granulator and were then mixed by stirring with 41.5 parts of acetic acid added thereto. The first composition consequently obtained was found to have a particle size distribution as follows.

| Mesh | % |
|---|---|
| −12 | 1.20 |
| 12–32 | 10.23 |
| 32–48 | 17.21 |
| 48–80 | 40.32 |
| 80–150 | 26.87 |
| 150− | 4.17 |
| Average particle diameter | 40–80 meshes |

Separately, powdery sodium hydrogen carbonate was prepared as the second composition.

EXAMPLE 9

The first composition obtained in Example 2 was placed, as not accompanied with any desiccator, in a bag made of a laminate film obtained by superposing polyethylene terephthalate (12 μm), polyethylene (15 μm), aluminum foil (7 μm), and polyethylene (30 μm) layers and tested for stability in storage at 40° C. The results were as shown in Table 4.

TABLE 4

| Item | 0 month | 1 month | 2 months |
|---|---|---|---|
| Color difference (ΔE) | 0.00 | 9.77 | 14.99 |
| Residual ratio of acetic acid ion (%) | 100.0 | 98.9 | 98.9 |
| Occurrence of aggregation | | Yes | Yes |

The "color difference (ΔE)" represents the numerical value (absolute number) determined by the use of a colorimetric system (produced by Minolta Camera K.K. and marketed under product code of "CD-200"). The "residual ratio of acetic acid ion" represents the magnitude determined by dissolving part of a sample in water and examining the resultant aqueous solution by high-speed liquid chromatography (by the use of a system produced by Nippon Bunko K.K. and marketed under product code of "BIP-I").

EXAMPLE 10

The first composition obtained in Example 8 was placed in combination with silica gel as a desiccant in a bag made of a laminate film obtained by superposing polyethylene terephthalate (12 μm), polyethylene (15 μm), aluminum foil (7 μm), and polyethylene (30 μm) layers and tested for stability in storage at 40° C. The results were as shown in Table 5.

TABLE 5

| Item | 0 month | 1 month | 2 months |
|---|---|---|---|
| Color difference (ΔE) | 0.00 | 0.52 | 0.92 |

TABLE 5-continued

| Item | 0 month | 1 month | 2 months |
|---|---|---|---|
| Residual ratio of acetic acid ion (%) | 100.0 | 98.9 | 98.9 |
| Occurrence of aggregation | | No | No |

EXAMPLE 11

The first composition obtained in Example 7, a composition produced by following the procedure of Example 7 except that the addition of sodium acetate was omitted (composition of Control 3), and a mixture of 2188.7 parts of sodium chloride and 41.5 g of acetic acid (composition of Control 4) were left standing in the open air at 30° C. for 30 minutes and then tested for residual ratio of acetic acid. The results were as shown in Table 6.

TABLE 6

| | Composition of | | |
|---|---|---|---|
| Time | Example 1 | Control 1 | Control 2 |
| Immediately after production | 100% | 100% | 100% |
| After 30 minutes following production | 100.2% | 17.6% | 12.7% |

It is clearly noted from Table 6 that the preparations for blood dialysis according with the present invention show specific adsorption of acetic acid by sodium acetate and excel in stability in preservation.

EXAMPLE 12

In a vertical granulator (stirring and mixing device produced by Fuji Sangyo K.K. and marketed under product code of "VG-25P"), 2188.7 parts of sodium chloride, 52.2 parts of potassium chloride, 77.2 parts of calcium chloride [$CaCl_2 \cdot 2H_2O$], 35.6 parts of magnesium chloride [$MgCl_2 \cdot 6H_2O$], 175.3 parts of sodium acetate, and 521.5 parts of glucose were mixed by stirring. Then, the resultant mixture was pulverized with a pin mill (pulverizing device produced by Fuji Sangyo K.K. and marketed under trademark designation of "Kollplex 16Z") and the resultant powder was mixed by stirring with the vertical granulator. The resultant mixture was pelletized with a roller compacter (dry granulating device produced by Turbo Kogyo K.K. and marketed under product code of "WP-160X60"). The granules and 41.5 parts of acetic acid added thereto were mixed by stirring with the vertical granulator. The first composition consequently obtained was found to have a particle size distribution as follows.

| Mesh | % |
|---|---|
| -12 | 0.20 |
| 12-32 | 47.11 |
| 32-48 | 16.35 |
| 48-80 | 7.29 |
| 80-150 | 5.38 |
| 150- | 23.17 |

EXAMPLE 13

An aqueous solution was obtained by dissolving 52.2 parts of potassium chloride, 77.2 parts of calcium chloride $CaCl_2 \cdot 2H_2O$], 175.3 parts of sodium acetate, and 35.6 parts of magnesium chloride [$MgCl_2 \cdot 6H_2O$] in 1500 parts of water (about 3 times the amount of the electrolytes). Separately, 2188.7 parts of sodium chloride and 525 parts of glucose were mixed by stirring with the vertical granulator. The resultant mixture was fluidized within a fluidized-bed pelletizer (produced by Fuji Sangyo K.K. and marketed under product code of "STREA-15"). The fluidized bed of the powder was sprayed with the aforementioned aqueous solution to gain in weight. The granules thus obtained placed in the vertical granulator and mixed by stirring with 41.5 parts of acetic acid added thereto. The first composition consequently obtained was found to have a particle size distribution as follows.

| Mesh | % |
|---|---|
| -12 | 0.82 |
| 12-32 | 8.78 |
| 32-48 | 15.57 |
| 48-80 | 44.14 |
| 80-150 | 25.74 |
| 150- | 4.76 |

EXAMPLE 14

A mixed powder comprising of 750 parts of sodium hydrogen carbonate and 40.0 parts of sodium acetate [$CH_3COONa \cdot 3H_2O$] was mixed by stirring with the vertical granulator. The resultant mixture was pelletized with a roller compacter. The second composition consequently obtained was found to have a particle size distribution as follows.

| Mesh | % |
|---|---|
| -12 | 6.23 |
| 12-32 | 30.11 |
| 32-48 | 15.87 |
| 48-80 | 10.69 |
| 80-150 | 4.80 |
| 150- | 32.30 |

EXAMPLE 15

The first and second compositions obtained in Examples 13 and 14 were separately placed, as not accompanied by any desiccator, in bags made of a laminate film obtained by superposing polyethylene terephthalate (12 $\mu$m), polyethylene (15 $\mu$m), aluminum foil (7 $\mu$m), and polyethylene (30 $\mu$m) layers and tested for stability in storage at 40° C. The results were as shown in Table 7.

TABLE 7

| Item | 0 month | 1 month | 2 months |
|---|---|---|---|
| First composition | | | |
| Color difference ($\Delta E$) | 0.00 | 0.05 | 0.11 |
| Residual ratio of acetic acid ion (%) | 100.0 | 99.9 | 99.7 |
| Occurrence of aggregation | | No | No |
| Second composition | | | |
| Color difference ($\Delta E$) | 0.00 | 0.03 | 0.05 |
| Occurrence of aggregation | | No | No |

The "color difference ($\Delta E$)" represents the numerical value (absolute number) determined by the use of a colorimetric system (produced by Minolta Camera K.K. and marketed under product code of "CD-200"). The "residual ratio of acetic acid ion" represents the magnitude determined by dissolving part of a sample in water and examining the resultant aqueous solution by high-speed liquid chromatography (by the use of a system produced by Nippon Bunko K.K. and marketed under product code of "BIP-I").

EXAMPLE 16

In a vertical granulator (stirring and mixing device produced by Fuji Sangyo K.K. and marketed under product code of "VG-25P"), 1038.6 parts of sodium chloride, 52.2 parts of potassium chloride, 77.2 parts of calcium chloride [$CaCl_2 \cdot 2H_2O$], 35.6 parts of magnesium chloride [$MgCl_2 \cdot 6H_2O$], 175.3 parts of sodium acetate [$CH_3COONa \cdot 3H_2O$], and 525 parts of glucose were mixed by stirring. The resultant mixture was then pulverized with a pin mill (pulverizing device produced by Fuji Sangyo K.K. and marketed under trademark designation of "Kollplex 16Z"). The resultant powder was further mixed by stirring with the vertical granulator. The mixture consequently obtained was pelletized with a roller compacter (dry granulating device produced by Turbo Kogyo K.K. and marketed under product code of "WP-160X60"). The granules and 41.5 parts of acetic acid added thereto were mixed by stirring with the vertical granulator. The first composition obtained as the result was found to have a particle size distribution as follows.

| Mesh | % |
| --- | --- |
| -12 | 3.25 |
| 12-32 | 24.38 |
| 32-48 | 26.71 |
| 48-80 | 9.21 |
| 80-150 | 5.51 |
| 150- | 30.94 |

EXAMPLE 17

An aqueous solution was obtained by dissolving 52.2 parts of potassium chloride, 77.2 parts of calcium chloride [$CaCl_2 \cdot 2H_2O$], and 290.8 parts of sodium acetate [$CH_3COONa \cdot 3H_2O$] in 1500 parts of water. Separately, 1038.6 parts of sodium chloride and 525 parts of glucose were mixed by stirring with the vertical granulator. The resultant mixture was fluidized within a fluidized-bed pelletizer (produced by Fuji Sangyo K.K. and marketed under product code of "STREA-15"). The fluidized bed of the powder was sprayed with the aforementioned aqueous solution to gain in weight. The granules obtained as described above were placed in the vertical granulator and were mixed by stirring with 41.5 parts of acetic acid added thereto. The first composition consequently obtained was found to have a particle size distribution as follows.

| Mesh | % |
| --- | --- |
| -12 | 2.37 |
| 12-32 | 9.36 |
| 32-48 | 16.81 |
| 48-80 | 43.44 |
| 80-150 | 23.98 |
| 150- | 4.04 |

EXAMPLE 18

A mixed powder comprising 750 parts of sodium hydrogen carbonate, 40.4 parts of sodium acetate [$CH_3COONa \cdot 3H_2O$], and 1150.0 parts of sodium chloride was mixed by stirring with the vertical granulator. The resultant mixture was pelletized with the roller compacter. The second composition consequently obtained was found to have a particle size distribution as follows.

| Mesh | % |
| --- | --- |
| -12 | 7.12 |
| 12-32 | 32.48 |
| 32-48 | 20.77 |
| 48-80 | 7.51 |
| 80-150 | 4.53 |
| 150- | 27.59 |

Control 5

A first composition obtained by following the procedure of Example 13 except that the addition of sodium acetate was omitted and a second composition was obtained by following the procedure of Example 14 except that the amount of sodium acetate added was changed to 215.3 parts were separately placed in the same packing material as used in Example 15 and tested for stability in storage at 40° C. The results were as shown in Table 8.

It is clearly noted from Table 8 that the compositions according with the present invention excelled those of Control 5 in terms of coloration, aggregation, and residual ratio of acetic acid ion.

TABLE 8

| Item | 0 month | 1 month | 2 months |
| --- | --- | --- | --- |
| First composition | | | |
| Color difference ($\Delta E$) | 0.00 | 0.69 | 2.07 |
| Residual ratio of acetic acid ion (%) | 100.0 | 87.6 | 76.5 |
| Occurrence of aggregation | | Yes | Yes |
| Second composition | | | |
| Color difference ($\Delta E$) | 0.00 | 0.07 | 0.19 |
| Occurrence of aggregation | | Yes | Yes |

The "color difference ($\Delta E$)" represents the numerical value (absolute number) determined by the use of a colorimetric system (produced by Minolta Camera K.K. and marketed under product code of "CD-200"). The "residual ratio of acetic acid ion" represents the magnitude determined by dissolving part of a sample in water and examining the resultant aqueous solution by high-speed liquid chromatography (by the use of a system produced by Nippon Bunko K.K. and marketed under product code of "BIP-I").

The preparation for blood dialysis according with the present invention, as described above, comprises two compositions, i.e. a first powdery composition comprising solid electrolytes for dialysis and a liquid acid and a second powdery composition comprising sodium hydrogen carbonate and glucose. It is, therefore, notably light as compared with the conventional dialytic liquid. When acetic acid is used as the liquid acid meant as a pH-adjusting agent, the preparation enjoys the advantage that it exhibits highly satisfactory stability in protracted preservation because the acetic acid impregnates the solid electrolyte particles containing the aforementioned acetate.

The preparation for blood dialysis according with the present invention is extremely light as compared with the conventional dialytic solution because it comprises two compositions, i.e. a first powdery composition comprising solid electrolytes for dialysis, glucose, and a liquid acid and a second powdery composition comprising sodium hydrogen carbonate. When acetic acid is used as the liquid acid meant as a pH-adjusting agent, the preparation enjoys the advantage that it exhibits highly satisfactory stability in protracted preservation because the acetic acid is specifically adsorbed by the sodium acetate in the solid electrolytes.

Further, since the preparation for blood dialysis is contained in combination with a desiccant in a moistureproof packing material, it has the advantage that it is retained very stably in the state of low moisture.

Further, the preparation for blood dialysis according with the present invention comprises two compositions, i.e. a first powdery composition comprising solid inorganic salts for dialysis, glucose, sodium acetate, and acetic acid and a second powdery composition comprising sodium hydrogen carbonate and sodium acetate, and is extremely light as compared with the conventional dialytic solution. This preparation further enjoys the advantage that it exhibits highly satisfactory stability in protracted storage and excels in the ease of use because acetic acid is used as the liquid acid meant as a pH-adjusting agent and is allowed to impregnate the solid inorganic salt particles containing the aforementioned acetate.

It has been found incredibly that the stability of the preparation is invariably high when sodium chloride is incorporated in the first composition or in the second composition. This freedom as to the incorporation of the sodium chloride allows the contents of sodium chloride in the first composition and the second composition to approximate to each other to the greatest possible extent and obviates the necessity for using different devices in dissolving the two compositions of the preparation. Thus, the prevent invention contributes to simplifying the equipment required in putting the preparation to use.

The preparation for blood dialysis according with the present invention is produced by the dry method or the fluidized-bed method. In spite of the use of calcium chloride or magnesium chloride, a substance which has heretofore defied uniform pulverization because of an excessively high deliquescing property, the powdery compositions of the preparation can be homogenized. Further, the problem that the components of the compositions cannot be easily distributed uniformly can be precluded by the aforementioned method of production.

What is claimed is:

1. A preparation for blood dialysis comprising a first powdery composition comprising solid electrolytes for dialysis and a pH adjusting agent and a second composition comprising sodium hydrogen carbonate and glucose.

2. A preparation according to claim 1, wherein said pH adjusting agent is acetic acid.

3. A preparation according to claim 2, wherein said acetic acid has impregnated granules of said solid electrolytes for dialysis containing an acetate.

4. A preparation according to claims 1, 2 or 3, which on being dissolved in a prescribed amount of water produces the following components of said solid electrolytes for dialysis and pH adjusting agent from said first composition:

| | |
|---|---|
| $Na^+$ | 90 to 140 mmols |
| $K^+$ | 0 to 4 mmols |
| $Ca^{++}$ | 0.5 to 2.2 mmols |
| $Mg^{++}$ | 0.2 to 1.0 mmol |
| $Cl^-$ | 90 to 140 mmols |
| $CH_3COO^-$ | 6 to 15 mmols | and the following components of sodium hydrogen carbonate and glucose from said second composition:

| | |
|---|---|
| $Na^+$ | 15 to 40 mmols |
| $HCO_3^-$ | 15 to 40 mmols |
| Glucose | 4 to 12 mmols. |

5. A preparation according to claim 1, wherein said second solid composition for dialysis is contained in combination with a desiccant in a moistureproof packing material having a moisture permeability (20° C.) of not more than 2.0 g/m²·24hrs.

6. A preparation according to claim 1, wherein said first solid composition for dialysis is contained in combination with a desiccant in a moisture proof packing material having a moisture permeability (20° C.) of not more than 2.0 g/m²·24hrs.

7. A method for the production of a preparation for blood dialysis comprising a first powdery composition comprising solid electrolytes for dialysis and a pH adjusting agent and a second composition comprising sodium hydrogen carbonate and glucose, which method comprises producing said first composition by mixing the components of said solid electrolytes for dialysis, pulverizing and then granulating the resultant mixture, and then mixing the resultant granules with said pH adjusting agent.

8. A method for the production of a preparation for blood dialysis comprising a first powdery composition comprising solid electrolytes for dialysis and a pH adjusting agent and a second composition comprising sodium hydrogen carbonate and glucose, which method comprises producing said first composition by spraying an aqueous solution of the components of said solid electrolytes for dialysis other than sodium chloride into a fluidized bed formed of sodium chloride powder and, at the same time, granulating the wet sodium chloride powder, and mixing the resultant granules with said pH adjusting agent.

9. A method according to claim 7 or claim 8, wherein said second composition undergoes granulation subsequently to said mixture of the powder of glucose with sodium hydrogen carbonate.

10. A preparation for blood dialysis comprising a first powdery composition comprising solid electrolytes for dialysis, glucose, and a pH adjusting agent and a second powdery composition comprising sodium hydrogen carbonate.

11. A preparation according to claim 10, where said pH adjusting agent is acetic acid.

12. A preparation according to claim 11, wherein said acetic acid is specifically adsorbed by granules of said solid electrolytes for dialysis containing sodium acetate.

13. A preparation according to claims 10, 11 or 12, which on being dissolved in a prescribed amount of water produces the following components of solid electrolytes for dialysis, glucose, and pH adjusting agent from said first composition:

| | |
|---|---|
| $Na^+$ | 90 to 140 mmols |
| $K^+$ | 0 to 4 mmols |
| $Ca^{++}$ | 0.5 to 2.2 mmols |
| $Mg^{++}$ | 0.2 to 1.0 mmols |

| | |
|---|---|
| Cl⁻ | 90 to 140 mmols |
| CH₃COO⁻ | 6 to 15 mmols |
| Glucose | 4 to 12 mmols | and the following components of sodium hydrogen carbonate from said second composition:

| | |
|---|---|
| Na⁺ | 15 to 40 mmols |
| HCO₃⁻ | 5 to 40 mmols. |

14. A preparation according to claims 10, 11 or 12, wherein said first composition is contained in combination with a desiccant and said first composition and said desiccant are contained in a moisture proof packing material having moisture permeability (20° C.) of not more than 2.0 g/cm²·24hrs.

15. A method for the production of a preparation for blood dialysis comprising a first powdery composition comprising solid electrolytes for dialysis, glucose, and a pH adjusting agent and a second powdery composition comprising sodium hydrogen carbonate, which method comprises producing said first composition by mixing the components of said solid electrolytes for dialysis and glucose, pulverizing and then granulating the resultant mixture, and then mixing the resultant granules with said pH adjusting agent.

16. A method for the production of a preparation for blood dialysis comprising a first powdery composition comprising solid electrolytes for dialysis, glucose, and a pH adjusting agent and a second powdery composition comprising sodium hydrogen carbonate, which method comprises producing said first composition by spraying an aqueous solution of the components of said solid electrolytes for dialysis other than sodium chloride into a fluidized bed of the mixed powder of sodium chloride and glucose and, at the same time, granulating the wet mixed powder, and mixing the resultant granules with said pH adjusting agent.

17. A preparation for blood dialysis, comprising a first powdery composition comprising solid inorganic salts for dialysis, glucose, sodium acetate, and acetic acid and a second powdery composition comprising sodium hydrogen carbonate and sodium acetate.

18. A preparation according to claim 17, which on being dissolved in a prescribed amount of water produces the following components of said solid inorganic salts for dialysis, glucose, sodium acetate, and acetic acid from said first composition:

| | |
|---|---|
| Na⁺ | 85 to 135 mmols |
| K⁺ | 0 to 4 mmols |
| Ca⁺⁺ | 0.5 to 2.2 mmols |
| Mg⁺⁺ | 0.2 to 1.0 mmol |
| Cl⁻ | 90 to 140 mmols |
| CH₃COO⁻ | 6 to 15 mmols |
| Glucose | 4 to 12 mmols | and the following components of sodium hydrogen carbonate and sodium acetate from said second composition:

| | |
|---|---|
| Na⁺ | 15 to 40 mmols |
| HCO₃⁻ | 15 to 40 mmols |
| CH₃COO⁻ | 0.5 to 3 mmols. |

19. A preparation according to claim 17, wherein said second composition further comprises sodium chloride.

20. A preparation according to claim 17, which on being dissolved in a prescribed amount of water produces the following components of said solid inorganic salts for dialysis, glucose, sodium acetate, and acetic acid from said first composition:

| | |
|---|---|
| Na⁺ | 6 to 135 mmols |
| K⁺ | 0 to 4 mmols |
| Ca⁺⁺ | 0.5 to 2.2 mmols |
| Mg⁺⁺ | 0.2 to 1.0 mmol |
| Cl⁻ | 4 to 140 mmols |
| CH₃COO⁻ | 4 to 10 mmols | and the following components of sodium hydrogen carbonate, sodium acetate, and sodium chloride from said second composition:

| | |
|---|---|
| Na⁺ | 15 to 135 mmols |
| HCO₃⁻ | 1 to 120 mmols |
| HCO₃⁻ | 15 to 40 mmols |
| CH₃COO⁻ | 0.5 to 3 mmols. |

21. A method for the production of a preparation for blood dialysis, comprising a first powdery composition comprising solid inorganic salts for dialysis, glucose, sodium acetate, and acetic acid and a second powdery composition comprising sodium hydrogen carbonate and sodium acetate, which method comprises producing said first composition by mixing the components of said solid inorganic salts for dialysis, sodium acetate, and glucose, pulverizing and then granulating the resultant mixture, and subsequently mixing the resultant granules with acetic acid.

22. A method for the production of a preparation for blood dialysis, comprising a first powdery composition comprising said solid inorganic salts for dialysis, glucose, sodium acetate, and acetic acid and a second powdery composition comprising sodium hydrogen carbonate and sodium acetate, which method comprises producing said first composition by spraying an aqueous solution of the components of said solid inorganic salts for dialysis excluding sodium chloride and containing or not containing sodium acetate into a fluidized bed of a mixed powder of sodium chloride and glucose and, at the same time, granulating the wet mixed powder and mixing the resultant granules with acetic acid.

23. A method according to claim 21 or claim 22, wherein said second composition is obtained by mixing sodium acetate powder or a mixed powder of sodium acetate and sodium chloride with sodium hydrogen carbonate and thereafter granulating the resultant mixture.

24. A preparation according to claim 1 wherein said pH adjusting agent is at least one member selected from the group consisting of acetic acid, lactic acid and hydrochloric acid.

25. A method according to claim 7 wherein said pH adjusting agent is at least one member selected from the group consisting of acetic acid, lactic acid and hydrochloric acid.

* * * * *